United States Patent [19]

Puckett et al.

[11] Patent Number: 5,268,470
[45] Date of Patent: Dec. 7, 1993

[54] DIAMINE COMPOUNDS, METHOD OF MAKING SAME, METHOD OF USE OF SAME AND INTERMEDIATES

[75] Inventors: Wallace E. Puckett; Mark L. Zollinger, both of Memphis, Tenn.

[73] Assignee: Buckman Laboratories Internation, Inc., Memphis, Tenn.

[21] Appl. No.: 728,688

[22] Filed: Jul. 12, 1991

[51] Int. Cl.$^5$ ............... C07D 337/02; C07D 281/02; C07D 267/08; C07D 247/00
[52] U.S. Cl. .................... 540/596; 540/597; 540/598; 544/87; 544/129; 544/141
[58] Field of Search ........... 540/596, 597, 598; 544/87, 129, 141

[56] References Cited

U.S. PATENT DOCUMENTS

| | | | |
|---|---|---|---|
| 3,366,631 | 1/1968 | Kalm | 544/71 |
| 4,026,935 | 5/1977 | Brennan et al. | 544/87 |
| 4,095,022 | 6/1978 | Brennan et al. | 544/87 |
| 4,117,227 | 9/1978 | Brennan | 544/170 |
| 4,247,482 | 1/1981 | Poppelsdorf | 564/508 |

FOREIGN PATENT DOCUMENTS

| | | |
|---|---|---|
| 2624016 | 12/1976 | Fed. Rep. of Germany . |
| 781407 | 8/1957 | United Kingdom . |
| 2045237 | 10/1980 | United Kingdom . |

OTHER PUBLICATIONS

Odian "Principles of Polymerization", 3rd ed. (1991) pp. 572-575.
Goethals et al., "The synthesis of block-copolymers . . . " in *Cationic Polymerization and Related Processes* (1984) pp. 388-394.
International Search Report, mailed Oct. 19, 1992.

*Primary Examiner*—Mukund J. Shah
*Assistant Examiner*—Matthew V. Grumbling
*Attorney, Agent, or Firm*—Finnegan, Henderson, Farabow, Garrett & Dunner

[57] ABSTRACT

A diamine useful as a catalyst for the polymerization of urethane. A method of making the catalyst comprises reacting a spiro quaternary amine with a secondary amine. The spiro quaternary amine is also useful as an antimicrobial agent.

29 Claims, No Drawings

DIAMINE COMPOUNDS, METHOD OF MAKING SAME, METHOD OF USE OF SAME AND INTERMEDIATES

BACKGROUND OF THE INVENTION

This invention relates to diamines which are suitable for use as urethane catalysts. The invention also relates to a method of making these compounds and to their use as catalysts and/or antimicrobial agents. The invention further relates to an intermediate compound which is used in the preparation of these catalysts. The invention also relates to a method of using such intermediates as antimicrobial agents.

Several spiro compounds are well-known and their preparation is mentioned in work by, for instance, Movsumzade et al., *Azerbaidzhanskii Khimicheskii Zhurnal*, vol. 3, pp. 53–8 and others.

The production of di-(N,N'-disubstituted amino) alkanes and their use as polyurethane catalysts, epoxy curing agents and as intermediates in the preparation of corrosion inhibitors, pharmaceuticals, emulsifiers, textile chemicals, rubber chemicals and the like are also generally well known. U.S. Pat. No. 4,103,087 teaches that di-(N,N'-disubstituted amino) alkanes may be prepared with high selectivity by use of a heterogeneous alumina phosphate catalyst. Prior art polyurethane catalysts include 2,2'-dimorpholinodiethylether (DMDEE).

The work cited in the prior art provides methods for preparing certain symmetrical diamines, but provides no suitable method for preparing unsymmetrical diamines.

SUMMARY OF THE INVENTION

A first embodiment of the present invention overcomes the problems and disadvantages of the prior art by providing a novel compound which is particularly suitable as a catalyst for the polymerization of urethane.

A second embodiment of the present invention overcomes the problems and disadvantages of the prior art by providing a high temperature method of preparing diamines and particularly unsymmetrical diamines. The diamines can be produced in high yield.

Additional objects and advantages of the invention will be set forth in part in the description that follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a first preferred embodiment of the present invention comprises a compound, preferably a catalyst for the polymerization of urethane, wherein the compound is represented by formula I $$R^3-CH-R^4-A-R^5-CH-R^6 \qquad I$$

wherein:

A represents S, O or $CH_2$; $R^1$ and $R^2$ each independently represents an alkyl group or may instead jointly represent a group of atoms which form a first heterocyclic ring, wherein the first ring is selected from piperidine, thiomorpholine, hexamethyleneimine and pyrrolidine, and wherein the first ring may have one or more alkyl substituents; $R^3$ and $R^6$ each independently represents hydrogen or an alkyl group; $R^4$ and $R^5$ each independently represents a bond or an alkylene group; $Z^1$ represents a group of atoms which form a second heterocyclic ring, wherein the second ring may be substituted or unsubstituted, wherein the second ring may be saturated or unsaturated and wherein the second heterocyclic ring may contain at least one heteroatom in addition to N.

Preferably, $R^3$ and $R^6$ both represent hydrogen and $R^4$ and $R^5$ both represent unbranched alkylene groups.

In a preferred embodiment, the first and second ring systems differ in structure and/or $R^3$ and $R^6$ differ in structure and/or $R^4$ and $R^5$ differ in structure. In other words, in a preferred embodiment, the diamine is unsymmetrical.

A second preferred embodiment of the present invention comprises a method of making a diamine represented by formula II $$R^3-CH-R^4-A-R^5-CH-R^6 \qquad II$$

, said method comprising:

contacting a spiro intermediate compound represented by formula III $$III$$

with a secondary amine of the formula $NHR^1R^2$ for a time sufficient to form the diamine II, wherein:

A represents S, O or $CH_2$; $R^1$ and $R^2$ each independently represents an alkyl group or may instead jointly represent a group of atoms which form a first heterocyclic ring, wherein the first ring may have one or more alkyl substituents; $X^-$ represents any suitable counterion, preferably a halogen; $R^3$ and $R^6$ each independently represents hydrogen or an alkyl group; $R^4$ and $R^5$ each independently represents a bond or an alkylene group; $Z^1$ represents a group of atoms which form a second heterocyclic ring, wherein the first and second rings may independently be substituted or unsubstituted, wherein the first and second rings may independently be saturated o unsaturated and wherein the second heterocyclic ring may contain at least one heteroatom in addition to $N^+$.

Preferably, $R^3$ and $R^6$ both represent hydrogen and $R^4$ and $R^5$ both represent unbranched alkylene groups.

In a preferred embodiment, the first and second ring systems differ in structure and/or $R^3$ and $R^6$ differ in structure and/or $R^4$ and $R^5$ differ in structure. In other words, in a preferred embodiment, the diamine is unsymmetrical.

It is possible to form unsymmetrical diamines from either symmetrical or unsymmetrical intermediates. It is likewise possible to form symmetrical diamines from either symmetrical or unsymmetrical intermediates.

A third preferred embodiment of the present invention comprises a spiro compound represented by the formula IV

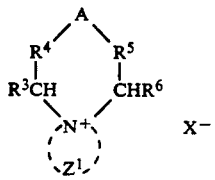

IV wherein:

$Z^{1\prime}$ represents a group of atoms which form a heterocyclic ring, wherein the ring may be substituted or unsubstituted, wherein the ring may be saturated or unsaturated and wherein the ring may contain one or more heteroatoms in addition to $N+$; $X^-$ represents a counter-ion, preferably a halogen; $R^3$ and $R^6$ each independently represents hydrogen or an alkyl group; $R^4$ and $R^5$ each independently represents a bond or an alkylene group; A represents S, O or $CH_2$, provided that when A represents $CH_2$, $Z^{1\prime}$ contains at least one heteroatom in addition to $N+$, and provided that when A represents O, $Z^{1\prime}$ does not represent a group of atoms which form morpholine.

The spiro compound III or IV may be formed by reacting a first compound having the formula V or VI

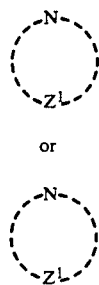

V or

VI with a second compound having the formula VII

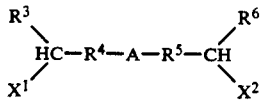

VII wherein $X^1$ and $X^2$ each independently represents a suitable counter-ion for the intermediate compound, wherein the counter-ion is preferably a halogen, and is more preferably chlorine or bromine, and wherein $R^3$, $R^4$, $R^5$, $R^6$, $Z^1$, $Z^{1\prime}$ and A are as defined above.

The second compound is preferably used in excess, and is more preferably in excess by a molar ratio of about 6:1. In a preferred embodiment, the second compound is also used as a solvent for the reaction. This is advantageous because it simplifies the process of separating the intermediate from the reaction medium. When the second compound is used as a solvent, it preferably may be reused to form subsequent batches of intermediate. If the solvent becomes contaminated, it may be distilled and then reused.

The reaction is preferably conducted at a temperature of between about 80° C. and 100° C. The total reaction time is preferably between about 2 and about 4 hours. The reaction time varies with the desired batch size.

The intermediate III or IV is also useful as an antimicrobial agent. It may be preferably used to inhibit the growth of bacteria and/or algae. The compounds of formulae I and II have at least one of the utilities described above for the di-(N,N'-disubstituted amino) alkanes.

In a preferred embodiment, 2,2'-dichlorodiethylether was reacted with morpholine to form 3,9-dioxa-6-azoniaspiro [5.5] undecane chloride as the intermediate.

In another preferred embodiment, 2,2'-dichlorodiethylether was reacted with 2,6-dimethyl morpholine to form 3,9-dioxa-8,10-dimethyl-6-azoniaspiro [5.5] undecane chloride as the intermediate.

In a preferred embodiment, 3,9-dioxa-6-azoniaspiro [5.5] undecane chloride was reacted with 2,6-dimethyl morpholine to form 2-(N-morpholino)-2'-[N-(2,6-dimethyl) morpholino] diethyl ether.

In another preferred embodiment, 3,9-dioxa-8,10-dimethyl-6-azoniaspiro [5.5] undecane chloride was reacted with morpholine to form 2-(N-morpholino)-2'-[N-(2,6-dimethyl)morpholino] diethyl ether.

To produce the diamine of the present invention, the intermediate III produced as described above is then further reacted with a secondary amine. The secondary amine is preferably selected from piperidine, 3-methylpiperidine, morpholine, 2,6-dimethyl morpholine, thiomorpholine, diethylamine, hexamethyleneimine, and pyrrolidine.

The reaction is preferably carried out in the presence of excess secondary amine. This secondary amine relative to the intermediate is more preferably present in a molar ratio of about 4:1.

In a preferred embodiment, the secondary amine is used as a solvent for the reaction. It may be recycled in the manner described above in connection with the formation of the intermediate.

The reaction is preferably carried out at a temperature of about 200° C. The total reaction time is preferably about 4 hours.

DESCRIPTION OF THE PREFERRED EMBODIMENTS

Reference will now be made in detail to the present preferred embodiments of the invention. In the examples and throughout the specification and claims, all parts and percentages are by weight unless otherwise specified.

EXAMPLES

The invention will be further clarified by the following examples, which are intended to be merely illustrative of the present invention. Unless otherwise specified, in each of the reactions described in the examples, a nitrogen blanket was used to exclude oxygen.

EXAMPLE 1

1420 grams of 2,2'-dichlorodiethylether were added to a 2 L, three neck flask, with reflux condenser, thermometer, and mechanical mixer. Mixing was begun and the reactor vessel was heated to 80° C. At this time, 174 grams of morpholine were added portion-wise, in such a manner that the temperature did not rise above 100° C. After the addition of morpholine, mixing was continued for another 2 hours.

The resulting solid was filtered through a large Buchner funnel, the solid was washed with two portions of a KOH/isopropanol solution, and then dried in a vacuum dessicator at 100° C. at 0.1 atmospheres for 2 hours to afford 220 grams of 3,9-dioxa-6-azoniaspiro [5.5] undecane chloride:

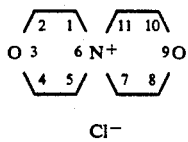

EXAMPLE 2

1400 grams of 2,5-dichloropentane were added to a 2 L, three neck flask, with reflux condenser, thermometer, and mechanical mixer. Mixing was begun and the reactor vessel was heated to 80° C. At this time, 174 grams of 3-methyl piperidine were added portion-wise, in such a manner that the temperature did not rise above 100° C. After the addition of 3-methyl piperidine, mixing was continued for another 2 hours.

The resulting solid was filtered through a large Buchner funnel, and dried in an evaporated dessicator at 100° C. at 0.1 atmospheres for 2 hours to afford 270 grams of 2-methyl-6-azoniaspiro [5.5] undecane chloride:

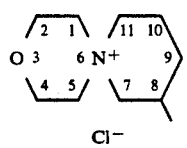

EXAMPLE 3

1420 grams of 2,2'-dichlorodiethylether were added to a 2 L, three neck flask with reflux condenser, thermometer, and mechanical mixer. Mixing was begun and the reactor vessel was heated to 80° C. At this time, 198 grams of 3-methyl piperidine were added portion wise, in such a manner that the temperature did not rise above 100° C. After the addition of 3-methyl piperidine, mixing was continued for another 2 hours.

The resulting solid was filtered through a large Buchner funnel, and dried in an evaporated dessicator at 100° C. at 0.1 atmospheres for 2 hours to afford 270 grams of 3-oxa-8-methyl-6-azoniaspiro [5.5] undecane chloride:

EXAMPLE 4

2.06 grams of thiomorpholine, 3.18 grams of 2,2' dichloro ethyl sulfide, 1.30 grams of potassium carbonate and 50 milliliters of ethanol were added to a 100 milliliter single-neck flask equipped with a reflux condenser. The resulting solution was then heated to reflux and mixed for 4 hours. The flask was then allowed to cool to room temperature and the solution was filtered through a paper filter. The ethanol solvent was removed in vacuo at 50° C. The solid material was washed in 10 milliliters of dichloromethane to remove excess 2,2'-dichloro ethyl sulfide and the solvent was removed by filtration through a paper filter to afford 2.6 grams of an off-white crystalline solid comprising 3,9-dithio-6-azoniaspiro [5.5] undecane chloride:

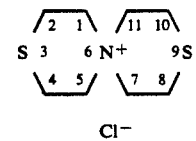

EXAMPLE 5

384 grams of 3,5-dimethyl-pyrazole, 2860 milliliters of 2,2'-dichlorodiethylether and 1.8 liters of ethanol were added to a 5 liter three-neck flask. The resulting solution was stirred mechanically and heated to reflux for 4 hours. The solution was then cooled to room temperature, thereby forming a precipitate. The precipitate was suction filtered and dried in a vacuum desiccator. The precipitate contained a compound represented by the formula:

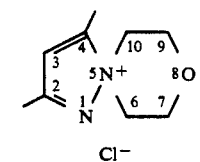

EXAMPLE 6

435 milliliters of morpholine and 2.5 liters of ethanol were added to a 4 liter resin pot equipped with a mechanical mixer, thermometer, and a reflux condenser. Mixing was begun and 715 grams of 2,2'-dichlorodiethylether were then added. The solution was heated to reflux and heating was continued for 2 hours. Next 1 liter of ethanol was distilled from the pot and was used to dissolve 325 grams of KOH having an purity of about 80-85%. The resulting ethanolic KOH solution was then added to the resin pot. A white precipitate formed almost immediately. The solution was then cooled to room temperature and suction filtered. Excess ethanol was then removed from the supernatent solution. The resulting brown solution having a suspended solid was poured into one liter of toluene, stirred for 30 minutes, suction filtered and washed with 2×100 milliliters of toluene. The resulting white solid was dried using an evacuated desiccator. The solid comprised 350 grams of 72.6% pure 3,9-dioxa-6-azoniaspiro [5.5] undecane chloride.

EXAMPLE 7

183 grams of morpholine and 2.5 liters of ethanol were combined in the apparatus described in Example 6 above. Mixing was begun and 382 grams of 2,2' dichloro ethyl sulfide were then added. The solution was heated to reflux and heating was continued for 2 hours. Next, 1 liter of ethanol was distilled from the pot and was used to dissolve 136.5 grams of KOH (80-85% pure). The ethanolic KOH solution was then added to the resin pot. Processing was continued using the step described in Example 6 above. After washing with toluene, a viscous brown liquid was obtained. Toluene was decanted and the viscous brown layer was evaporated in vacuo at 70° C. to afford a viscous brown liquid which later solidified. The viscous brown liquid contained a compound represented by the formula:

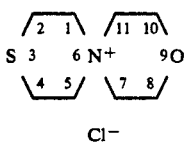

Cl⁻

EXAMPLE 8

588 grams of hexamethyleneimine, commercially available from Dupont, and 2 liters of reagent grade ethanol were added to a 5 liter three-neck flask having a mechanical mixer, reflux condenser, thermometer and dropping funnel. The resulting solution was mixed and heated to reflux. 858 grams of 2,2'-dichlorodiethylether were then slowly added to the solution. The addition step lasted about 1 hour. Next, the solution was heated for 2 hours. A solution containing 390 grams of KOH diluted to 1500 milliliters with ethanol was then added in one portion. This resulted in the formation of a white precipitate. The solution was then cooled to room temperature, suction filtered, evaporated in vacuo, washed with 1 liter of ethyl acetate with agitation, suction filtered, washed again with 1 liter of ethyl acetate, again suction filtered, and dried in an evacuated oven overnight at 50° C. and 0.1 atmosphere. 430 grams of a white solid resulted. The white solid contained a compound represented by the formula:

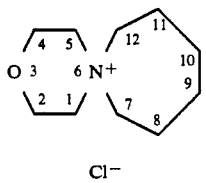

Cl⁻

EXAMPLE 9

1.4 liters of a solution comprising ethanol and 325 grams of 85% pure KOH were added to a 4 liter resin pot equipped with a mechanical mixer, and a reflux condenser. 580 milliliters of 2,6-dimethylmorpholine and 590 milliliters of 2,2'-dichlorodiethylether were added to the solution. A white precipitate formed almost immediately after mixing was begun. The temperature was raised to reflux for two hours. During this time, ethanol was added to maintain the level in the resin pot. The solution was then allowed to cool to room temperature. The solution was then suction filtered, evaporated in vacuo, washed with one liter of toluene, mixed with a mechanical mixer for 45 minutes and suction filtered. The resulting filtrate was dried in an evacuated desiccating oven at 100° C. and 0.1 atmosphere for one hour to provide 330 grams of 3,9-dioxa-2,4-dimethyl-6-azoniaspiro [5.5] undecane chloride

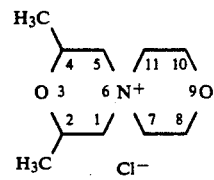

EXAMPLE 10

261 grams of morpholine, 1 liter of ethanol and 195 grams of KOH were added to a two liter three neck flask equipped with a mechanical mixer, reflux condenser, dropping funnel and thermometer. The solution was heated and mixed in order to dissolve the KOH. The solution was then heated to reflux and a very slow addition of 420 grams of 1,5-dichloropentane was begun via a dropping funnel. The addition step lasted about three hours. A white precipitate formed during the addition. After the addition, the solution was heated for one hour and allowed to cool to room temperature. The solution was then suction filtered, washed with toluene and dried in an evacuated desiccator for one hour to provide 250 grams of a white crystalline solid comprising 3-oxa-6-azoniaspiro [5.5] undecane chloride:

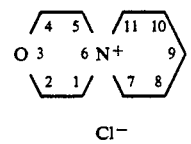

Cl⁻

EXAMPLE 11

12 pounds of 3,9-dioxa-6-azoniaspiro [5.5] undecane chloride and 25 pounds of hexamathyleneimine were added to a 10 gallon autoclave. The reactor was purged with nitrogen, sealed and heated to 200° C. at 125 psi for four hours. Upon cooling, the solution was then neutralized with anhydrous ammonia, suction filtered, evaporated in vacuo and distilled at 140°-160° C. and 0.5 mm Hg to provide approximately 1 liter of product comprising 2-(N-morpholino)-2'-(N-hexamethyleneimino) diethyl ether.

EXAMPLE 12

230 grams of 3,9-dioxa-6-azoniaspiro [5.5] undecane chloride and 450 milliliters of piperidine were added to a 1 liter autoclave bomb. The bomb was sealed. Mixing was begun and the bomb was heated to 200° C. for 4 hours. The bomb was then cooled by a water jacket to 70° C. This resulted in the formation of an off-white crystalline material. The resulting suspension was neutralized with a solution of 100 grams of KOH dissolved in 500 milliliters of methanol. After mixing with KOH/methanol for 30 minutes, the methanol was removed in vacuo and suction filtered, affording a light yellow liquid. The filter cake was washed with 2×100 milliliters of methanol, and the filtrates were combined. The methanol was removed in vacuo to afford a light yellow to amber liquid. The liquid was distilled at high vacuum to afford morpholine and then a fraction was collected which distilled at 140°-160° C. at 0.25 mm Hg. The resulting product comprised 2-(N-piperidine)-2'-(N-morpholino)-diethylether.

EXAMPLE 13

205 grams of 3-oxa-8-methyl-6-azoniaspiro [5.5] undecane chloride and 400 milliliters of hexamethyleneimine were added to the apparatus described in Example 12 above. Substantially the same procedure described in Example 12 was then followed. The final product was neutralized with a solution of 65 grams of KOH in 500 milliliters of ethanol. During neutralization, a precipitate formed and was later removed by filtration. The supernatent fluid was evaporated in vacuo, and the final solution was distilled at 140°-160° C. and 2 mm Hg to provide a light yellow solution comprising 2-(N-3-methyl piperidino)-2'-(N-hexamethyleneimino) diethylether.

EXAMPLE 14

400 milliliters of hexamethyleneimine and 120 grams of the intermediate formed in Example 7 were added to a 1 liter autoclave bomb. Substantially the same procedure described in Example 12 was followed. The product was neutralized with anhydrous ammonia. The resulting liquid was suction filtered, evaporated in vacuo and distilled at 100°-185° C. at 2 mm Hg to provide a medium yellow liquid comprising 2-(N-morpholino)-2'-(N-hexamethyleneimino)thioethylether.

EXAMPLE 15

200 grams of the intermediate described in Example 8 and 400 milliliters of hexamethyleneimine were added to a 1 liter autoclave bomb. Substantially the same procedure as described in Example 12 was followed. After completion of the reaction, the solution was stirred and anhydrous ammonia was bubbled through for 45 minutes. This solution was then suction filtered, evaporated in vacuo and distilled at 140°-165° C. at 0.5 mm Hg to provide a pale yellow liquid comprising 2,2'-(N,N'-bishexamethyleneimino) diethylether.

EXAMPLE 16

A 1 L autoclave bomb was charged with 200 grams of the intermediate product of example 1 and 500 milliliters of pyrrolidine. The autoclave bomb was sealed. Mixing was begun, and the reactor was heated to 200° C. for four hours. The resulting dark green liquid, containing an off white solid, was then neutralized with anhydrous ammonia, filtered, evaporated in vacuo at 80° C. at 0.1 atmospheres to remove excess pyrrolidine, and distilled through a short path distillation column at 145° C. at 2.0 mm Hg to afford 150 grams of a light yellow liquid, which later solidified to an off-white waxy solid comprising 2-N-morpholino-2'-N-pyrrolidino diethyl ether.

EXAMPLE 17

A 1 L autoclave bomb was charged with 200 grams of the intermediate product of example 1 and 500 milliliters of 3-methyl piperidine. The autoclave bomb was sealed. Mixing was begun, and the reactor was heated to 200° C. for four hours. The resulting dark green liquid, containing an off white solid, was then neutralized with anhydrous ammonia, filtered, evaporated in vacuo at 80° C. at 0.1 atmospheres to remove excess 3-methyl piperidine, and distilled through a short path distillation column at 145° C. at 2.0 mm Hg to afford 150 grams of a light yellow liquid comprising 2-(N-morpholino)-2'-(N-(3-methyl) piperidino) diethyl ether.

EXAMPLE 18

A 1 L autoclave bomb was charged with 200 grams of the intermediate product of example 3 and 500 milliliters of hexamethyleneimine. The autoclave bomb was sealed. Mixing was begun, and the reactor was heated to 200° C. for four hours. The resulting dark green liquid, containing an off white solid, was then neutralized with anhydrous ammonia, filtered, evaporated in vacuo at 80° C. at 0.1 atmospheres to remove excess hexamethyleneimine, and distilled through a short path distillation column at 145° C. at 2.0 mm Hg to afford 150 grams of a light yellow liquid comprising 2-(N-(3-methyl) piperidino)-2'-(N-hexamethyleneimino) diethyl ether.

EXAMPLE 19

A 1 L autoclave bomb was charged with 200 grams of the intermediate product of example 1 and 500 milliliters of hexamethyleneimine. The autoclave bomb was sealed. Mixing was begun, and the reactor was heated to 200° C. for four hours. The resulting dark green liquid, containing an off white solid, was then neutralized with anhydrous ammonia, filtered, evaporated in vacuo at 80° C. at 0.1 atmospheres to remove excess hexamethyleneimine, and distilled through a short path distillation column at 145° C. at 2.0 mm Hg to afford 150 grams of a light yellow liquid comprising 2-(N-morpholino)-2'-(N-hexamethyleneimino) diethyl ether.

EXAMPLE 20

1420 grams of 2,2'-dichlorodiethylether were added to a 2 L, three neck flask, with reflux condenser, thermometer, and mechanical mixer. Mixing was begun and the reactor vessel was heated to 80° C. At this time, 174 grams of morpholine were added portion-wise, in such manner that the temperature did not rise above 100° C. After the addition of morpholine, mixing was continued for another 2 hrs.

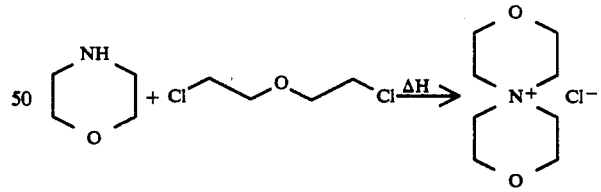

The resulting solid was filtered through a large Buchner funnel. The solid was washed with two portions of a KOH/isopropanol solution, and then dried in a vacuum desiccator a 100° C. at 0.1 atmospheres for 2 hrs. to afford 220 grams of 3,9-dioxa-6-azoniaspiro [5.5] undecane chloride.

A 1 L autoclave bomb was charged with 200 grams of 3,9-dioxa-6-azoniaspiro [5.5] undecane chloride produced by the above reaction. 500 milliliters of 2,6-dimethyl morpholine were also added. The autoclave bomb was sealed. Mixing was begun, and the reactor was heated to 200° C. for four hours.

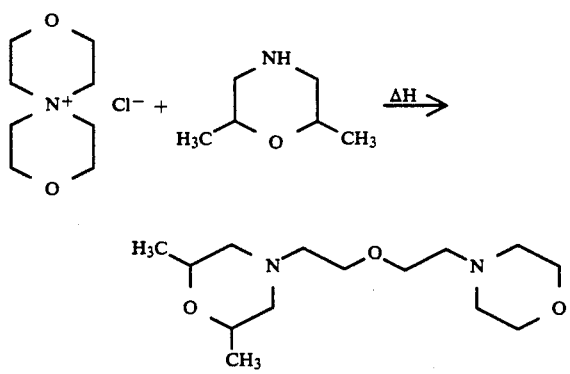

The resulting dark green liquid, containing an off white solid, was then neutralized with anhydrous ammonia, filtered, evaporated in vacuo at 80° C. at 0.2 atmospheres to remove excess 2,6-dimethyl morpholine, and distilled through a short path distillation column at 145° C. at 2.0 mm Hg to afford 196 grams of a light yellow liquid comprising 2-(N-morpholino)-2'-(N-(2,6-dimethyl) morpholino) diethyl ether.

EXAMPLE 21

The effect of 3,9-dioxa-6-azoniaspiro [5.5] undecane chloride produced in accordance with the method of Example 1 on the bacterium *Enterobacter aerogenes* was determined using the method described in U.S. Pat. No. 2,881,070, the disclosure of which is incorporated by reference. The results are described in Table 1.

TABLE 1

Concentration in parts per million required for 90 percent kill or greater of the compound of Example 1 against *Enterobacter aerogenes* and at pH 6 and pH 8 in a basal salt substrate after 18 hours contact.

| Bacterium | pH 6 | pH 8 |
|---|---|---|
| *Enterobacter aerogenes* | 100 | 100 |

EXAMPLE 22

The effect of 3,9-dioxa-6-azoniaspiro [5.5] undecane chloride, the composition described in Example 1, against algae was determined using the method described in U.S. Pat. No. 2,881,070 with the result as described in Table 2.

TABLE 2

Concentration in parts per million required for the compound of Example 1 to prevent the growth of *Chlorella pyrenoidosa* and at pH 7 in a basal salt substrate after 18 hours contact.

| | pH 7 |
|---|---|
| *Chlorella pyrenoidosa* | 100 |

EXAMPLE 23

The effect of the composition described in Example 17 against algae was determined using the method described in U.S. Pat. No. 2,881,070 with the result as described in Table 3.

TABLE 3

Concentration in parts per million of the compound in Example 1 required to prevent the growth of *Chlorella pyrenoidosa* and *Chlorcoccum hypnosporum* and at pH 7 in a basal salt substrate after 18 hours contact.

| | pH 7 |
|---|---|
| *Chlorella pyrenoidosa* | 1000 |
| *Chlorcoccum hypnosporum* | 1000 |

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

What is claimed is:

1. A method of making a diamine represented by formula II

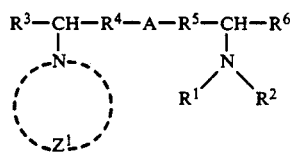

comprising:
contacting a spiro quaternary amine represented by formula III

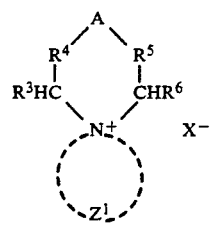

with a secondary amine of the formula $NHR^1R^2$ for a time sufficient to form the diamine II, wherein:

A represents S, O or $CH_2$;

$R^1$ and $R^2$ each independently represents an alkyl group or may instead jointly represent a group of atoms which, together with the nitrogen to which they are bonded, form a first heterocyclic ring, wherein said first heterocyclic ring is saturated or unsaturated, but not aromatic, and further is substituted or unsubstituted;

X represents a counter ion;

$R^3$ and $R^6$ each independently represents hydrogen or an alkyl group;

$R^4$ and $R^5$ each independently represents a bond or a branched or unbranched alkylene group, provided that $R^4$ and $R^5$ are not each a bond;

$Z^1$ represents a group of at least 4 atoms which, together with the nitrogen to which they are bonded, form a second heterocyclic ring, wherein said second heterocyclic ring is saturated or unsaturated, but not aromatic, and further is substituted or unsubstituted.

2. The method of claim 1, further comprising the step of recovering said diamine.

3. The method of claim 2, further comprising adding a base prior to recovering said diamine.

4. The method of claim 1, further comprising, prior to said contacting step, the step of reacting a heterocyclic amine of formula V

with a compound of formula VII

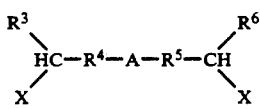

for a time sufficient to form said spiro quaternary amine.

5. The method of claim 4, wherein said compound of formula VII Is present in excess.

6. The method of claim 5, wherein the molar ratio of said compound of formula VII to said heterocyclic amine of formula V is about 6:1.

7. The method of claim 5, wherein said compound of formula VII is also the reaction solvent.

8. The method of claim 1, wherein said contacting occurs at a temperature of about 200° C.

9. The method of claim 1, wherein said secondary amine is present in excess.

10. The method of claim 9, wherein the molar ratio of said secondary amine to said spiro quaternary amine is about 4:1.

11. The method of claim 1, wherein said secondary amine also acts as the solvent for said reaction mixture.

12. The method of claim 40, wherein said diamine is recovered by distillation.

13. The method of claim 12, wherein said distillation is performed at reduced pressure.

14. The method of claim 1, wherein the rings of said spiro quaternary amine are each a 5-, 6- or 7-membered ring.

15. The method of claim 1, wherein $R^1$ and $R^2$ each independently represents a C1-C6 alkyl group.

16. The method of claim 1, wherein said first ring is saturated.

17. The method of claim 1, wherein said second ring is saturated.

18. The method of claim 1, wherein $R^3$ and $R^6$ both represent hydrogen.

19. The method of claim 18, wherein $R^4$ and $R^5$ both represent unbranched alkylene groups.

20. The method of claim 1, wherein $R^4$ and $R^5$ both represent unbranched alkylene groups.

21. The method of claim 1, wherein said diamine is selected from 2-N-morpholino-2'-N-pyrrolidino diethyl ether, 2-N-morpholino-2'-(N-(3-methyl) piperidino) diethyl ether, 2-(N-(3-methyl) piperidino)-2'-(N-hexamethyleneimino) diethyl ether, 2-piperidino-2'-morpholino diethyl ether, 2-(N-morpholino)-2'-(N-hexamethyleneimino) thioethylether, 2,2'-dihexamethyleneimino diethyl ether, 2-(N-morpholino)-2'-(N-hexamethyleneimino) diethyl ether and 2-morpholino-2'-(N-2,6-dimethyl morpholino) diethyl ether.

22. The method of claim 1, wherein said intermediate is selected from 3,9-dioxa-6-azoniaspiro [5.5] undecane chloride, 3-oxa-6-azoniaspiro [5.5] undecane chloride, 3-oxa-8-methyl-6-azoniaspiro [5.5] undecane chloride, 3,9-dithio-6-azoniaspiro [5.5] undecane chloride and 3,9-dioxa-2,4-dimethyl-6-azoniaspiro [5.5] undecane chloride.

23. The method of claim 1, wherein said intermediate is a substituted or unsubstituted 3,9-dioxa-6-azoniaspiro [5.5] undecane chloride.

24. The method of claim 23, wherein said intermediate has one or more C1-C6 alkyl substituents.

25. The method of claim 1, wherein said secondary amine is selected from piperidine, 3-methylpiperidine, morpholine, 2,6-dimethyl morpholine, thiomorpholine, diethylamine, hexamethyleneimine and pyrrolidine.

26. The method of claim 1, wherein the first and second ring systems differ in structure.

27. The method of claim 1, wherein $R^3$ and $R^6$ differ in structure.

28. The method of claim 1, wherein $R^4$ and $R^5$ differ in structure.

29. The method of claim 1, wherein X represents a halogen.

* * * * *